United States Patent [19]

Metcalfe et al.

[11] Patent Number: 4,539,294

[45] Date of Patent: Sep. 3, 1985

[54] IMMOBILIZATION OF PROTEINS ON POLYMERIC SUPPORTS

[75] Inventors: Lincoln D. Metcalfe, Lagrange; Dieter Frank, Naperville, both of Ill.

[73] Assignee: Akzona Incorporated, Enka, N.C.

[21] Appl. No.: 431,891

[22] Filed: Sep. 30, 1982

[51] Int. Cl.³ .................. C12N 11/08; C12N 11/02; C12N 11/06; C07G 7/00
[52] U.S. Cl. .................. 435/180; 260/112 R; 435/177; 435/181
[58] Field of Search ............... 435/174, 177, 178, 180, 435/181; 260/112 R

[56] References Cited

U.S. PATENT DOCUMENTS

| | | | |
|---|---|---|---|
| 3,841,969 | 10/1974 | Emery et al. | 435/178 X |
| 4,043,869 | 8/1977 | Barker et al. | 435/181 X |
| 4,072,566 | 2/1978 | Lynn | 435/176 |

FOREIGN PATENT DOCUMENTS 0131392 10/1980 Japan .................... 435/180

OTHER PUBLICATIONS

Zaborsky, O., Immobilized Enzymes, CRC Press, Cleveland, Ohio, 1973, (pp. 145–147).

*Primary Examiner*—David M. Naff
*Attorney, Agent, or Firm*—Francis W. Young; Louis A. Morris

[57] ABSTRACT

A protein is immobilized by a simple and effective method on a porous polymeric support by a first soaking in a dilute long-chain cationic solution and a second soaking in a dilute aqueous protein solution. The long chain cationic is preferably a nitrogen compound such as a diamine having at least one alkyl or alkenyl group containing at least eight carbon atoms. A preferred diamine is N-coco-1,3-diamino-propane. The protein may be an enzyme or hormone. A preferred enzyme is catalase or a two enzyme system of catalase and glucose oxidase.

28 Claims, No Drawings

IMMOBILIZATION OF PROTEINS ON POLYMERIC SUPPORTS

BACKGROUND OF THE INVENTION

This invention relates to the field of immobilizing proteins upon polymeric supports, particularly to the immobilization of enzymes upon porous polymeric materials.

Enzymes, the proteinaceous catalysts for many biological reactions, have wide use in the food and pharmaceutical industries. For example, glucose isomerase is used for the conversion of a glucose reaction mixture to fructose, lactase for the removal of lactose during the isolation of proteins from cheese whey, α-amylase and glucoamylase for the liquefaction and saccharification of corn starch to liquid syrup, and penicillin amidase to produce 6-aminopenicillanic acid from penicillin. The immobilization of enzymes on solid supports has advantages that have long been recognized. Upon treatment with the catalyst by passage of a mixture or substrate through the support, the immobilized enzyme remains bonded to the support rather than passing through with the substrate so that there is no need to recover the enzyme from the substrate and so that the enzyme remains in the support where it may be reused.

Prior art methods of immobilizing proteins on solid supports include that disclosed in U.S. Pat. No. 4,210,722, issued to Silver on July 1, 1980, and entitled "Protein Immobilizer", hereinafter referred to as Silver. Silver discloses a method of immobilizing a biologically active protein on a polar support by first applying to the support a monolayer or coating of a water-soluble polymer containing a β-hydroxylalkyleneamine moiety. The Silver method is somewhat disadvantageous in that the polymer must be deposited on the support to ensure enzyme immobilization.

U.S. Pat. No. 4,072,566, issued to Lynn on Feb. 7, 1978, and entitled "Immobilized Biologically Active Proteins", hereinafter referred to as Lynn, discloses a method of bonding enzymes or other biologically active proteins to an inorganic support material using p-phenylenediamine. The support materials disclosed as useful in the invention include siliceous materials, stannic oxide, titania, manganese dioxide, and zirconia. The only supports disclosed in the Examples were 40 to 80 mesh porous glass particles and 120 to 200 mesh porous silica. There is no disclosure in Lynn pertaining to immobilization of proteins upon organic supports such as those made from porous polymers.

U.S. Pat. No. 3,933,589, issued Jan. 20, 1976, to Keyes and entitled "Chemical Immobilization of Enzymes", discloses a method requiring a preformed reaction solution of an alkyl dihalide and an alkane diamine to effect the immobilization.

U.S. Pat. No. 4,251,631, issued Feb. 27, 1981, to Simon, and entitled "Cross-Linked Enzyme Membrane", discloses a method for the preparation of a cross-linked enzyme membrane by directly adsorbing enzymes into the pores of a microporous non-fibrous filter membrane made of a silica modified vinylchloride polymer and then cross-linking the enzyme with a bifunctional coupling agent whereby enzyme molecules are cross-linked to each other without chemically bonding the enzyme molecules to the membrane. The membranes required by the Simon invention are those having finely divided silicon dioxide embedded therein. Further, the cross-linking required by the Simon method requires treatment of the membrane with a cross-linking agent, as for example glutaraldehyde, dioxobenzidine, hexamethylenediisocyanate, or 1,5-difluoro-2,4-dinitrobenzene, after the immobilization of the enzyme on the silica-modified polymer. The enzyme may be immobilized on the silica-modified polymers of Simon prior to treatment of those polymers with a diamine. Immobilization on many other polymers is not possible without such treatment and the Simon process is thus unsuitable for immobilizing enzymes on those other polymers.

U.S. Pat. No. 3,841,969 issued Oct. 15, 1974 to Emery et al and entitled "Preparation of Immobilized Enzymes" discloses a method for preparing a water insoluble enzyme by reacting at a pH of 3 to 7 an enzyme with a titanium, tin, zirconium or iron derivative of a polysaccharide, nylon or glass. For example, a titanic chloride solution may be added to nylon fibers to form a suspension that is dried in an oven overnight. The resulting dry powder is washed three times with an acetate buffer and the buffer and powder separated by centrifugation. The enzyme is added to the resulting slurry and then the water insoluble enzyme formulation is washed with an acetate buffer and sodium chloride solution. Although this procedure is suitable for nylon fibers, it is not suitable for certain other supports that must be treated with a diamine rather than a metal salt before enzymes are successfully immobilized thereon.

U.S. Pat. No. 4,043,869 issued to Barker et al on Aug. 23, 1977 and entitled "Water-insoluble Biologically Active Material" discloses a method of securing enzymes upon water-insoluble solids. Such solids must first be treated with a diazotized N-diaminobenzene and the solids disclosed as suitable supports for the material include inorganics such as porous glass, porous silica and wood.

U.S. Pat. No. 4,204,041 was issued on May 20, 1980 to Bailey et al and is entitled "High Loading of Immobilized Enzymes on Activated Carbon Supports". The method of this invention appears to be suitable only for use with porous particles of activated carbon. The carbodiimides that act as immobilizing agents for the enzymes couple with carboxyl radicals on the surface of the activated carbon. Thus, support materials not having carboxyl radicals on their surface will not be suitably treated by these carbodiimides. Further, as disclosed in column 7 of Bailey, the immobilization is carried out over a period of twenty-four hours.

SUMMARY OF THE INVENTION

The present invention is a simple and effective method for immobilizing a protein on a polymeric support, comprising a first soaking step in which the support is placed in a dilute solution of a long-chain cationic surfactant in a solvent and a second soaking step in which the support is soaked in a dilute aqueous solution of the protein. During the first and second soaking steps, the dilute cationic-solvent solution is gently agitated.

In another aspect of the invention, the protein is an enzyme, the preferred solvent for the cationic surfactant is acetone, and the first soaking step is carried out over from 10 to 60 minutes while the second soaking step extends over a period in excess of four hours. Solutions of acetone and a long-chain cationic lead to supports having higher enzyme activities than supports treated with the same cationic and some otherwise suitable solvents. A still further aspect of the invention comprises the use of N-coco-1,3-diaminopropane, also preferable to alternatives in that treatment with that long-chain cationic, a diamine, leaves the support with a comparitively high enzyme activity. In yet another aspect of the invention, the enzyme is catalase.

DESCRIPTION OF THE PREFERRED EMBODIMENTS

The polymeric material upon which the enzyme is to be immobilized is preferably a porous polymer. The material may be a homopolymer of an olefin, such as low- or high-density polyethylene, polypropylene, or polymethylpentene, a homopolymer of a non-olefin such as Nylon 6, 11, or 66 and polycarbonate, or a copolymer. The material upon which the enzyme is to be immobilized may be of any convenient shape or form, such as for example a powder, film, tube, or rod. Suitable porous polymeric materials include Accurel® porous polymers, which are manufactured in powdered form by the Armak Company, 300 South Wacker Drive, Chicago, Ill. 60606, and in film form by Membrana, Inc., 7071 Commerce Circle, Pleasanton, Calif. 94566. Accurel® porous polymers are disclosed and thoroughly discussed in U.S. Pat. No. 4,247,498, issued to Castro on Jan. 27, 1981, which is incorporated by reference herein. Other porous polymers were also tested and some were found to be suitable supports for the invention.

The long-chain cationic treatment of the polymeric support in the first soaking step prepares the porous surface of the support for immobilization of the enzymes thereon. Herein, "long-chain cationics" refers to nitrogen compounds having at least an eight carbon alkyl or alkenyl group attached thereto, and includes amines, diamines, quaternary ammonium compounds, amido amines, and imidazolines. Among the preferred cationics the diamines are preferably diluted in a solvent to form a dilute diamine solution; the support is then soaked in this solution with gentle agitation. Other suitable cationics include nitrogen-containing compounds such as for example, o-hydroxy-benzylcocoamine, prepared in a Mannich reaction of phenol and cocoamine, which in dilute solutions were found to be suitable for enzyme immobilization. More preferred compounds for the preparation of dilute cationic solutions include the diamine, amine, and quaternary compounds, Duomeen® C, Armeen® C, and Arquad® 2C, respectively. Each of these compounds are products of the Armak Company, and are Armak's registered trademarks for N-coco-1,3-diamino-propane, cocoamine, and dimethyldicocoammonium chloride, respectively. A measure of preference for a pretreatment compound is the enzyme activity in the support after the second soaking step; higher enzyme activity translates into a more effective support in that more catalysis can occur thereon. One measure of activity for the enzyme catalase is the Baker, which is defined as the amount of catalase which catalyzes the decomposition of 264 mg of hydrogen peroxide under conditions of the assay, which in this case was 0.5M $H_2O_2$ at a pH of 7.0 for 60 minutes. Higher Bakers per unit area of a support corresponds to a higher catalytic potential. Thus, the compounds used in the first soaking step that result in a support having the highest activity in Bakers per unit area will be most preferred. Table I lists the catalase activity of several Accurel® porous polymer films treated in accordance with the present invention, the only variable being the amine, diamine, or quaternary ammonium compound used in the first soaking step. All of the Accurel® porous polymer films treated and whose results are shown in Table I were made of polypropylene:

TABLE I

| Cationic | Activity (Bakers/in$^2$ Accurel® Porous Polymer) |
| --- | --- |
| Duomeen® C | >13.0 |
| Armeen® C | 11.9 |
| Arquad® 2C | 11.2 |
| o-hydroxybenzylcocoamine | 7.9 |
| benzylcocoamine | 6.0 |
| Ethomeen® C/12[1] | 5.2 |
| Armeen® 2C[2] | 4.4 |
| Arquad® C-50[3] | 4.0 |
| Armeen® DMCD[4] | 2.9 |
| Aromox® DMMC-W[5] | 1.1 |

These trademarks are all registered by the Armak Company, 300 South Wacker Drive, Chicago, Illinois 60606:
[1]trademark for bis(2-hydroxyethyl)cocoamine
[2]trademark for dicocoamine
[3]trademark for trimethylcocoammonium chloride-50% active
[4]trademark for N,N—dimethylcocoamine
[5]trademark for dimethylcocoamine oxide(middle-cut coco fraction)

As demonstrated in the above table, all of the amines, diamines, and quaternary ammonium compounds tested, when used in the first soaking step, result in a support having active immobilized catalase. In contrast, an untreated porous polymer (polypropylene) film was found to have an activity of 0.1 Bakers.

The solvents for the cationic surfactant studied included methanol, isopropanol, chloroform, and acetone. Soaking in methanol solutions discolored the edges of the polypropylene film support, and thus methanol proved to be an unsuitable solvent. Isopropanol, chloroform, and acetone solutions were all satisfactory, but as chloroform-treated supports have higher catalase activities than isopropanol-treated polypropylene supports, chloroform is a preferred cationic solvent.

The treatment with a long-chain cationic in the first soaking step was equally effective whether the support was immersed for 5 minutes or 60 minutes; thus, 5 minutes is a preferred immersion time in the first soaking step. It is understood by those skilled in the art that the times disclosed as suitable herein for the first and second soaking steps are for normal room temperatures and atmospheric pressures, and that variations from these temperatures and pressures may change the preferred immersion times. It is further understood that the support may be immersed for even less than five minutes, the time of immersion required depending upon the cationic used and on other factors not fully understood. What is understood is that a determination as to the sufficiency of the immersion time in the first soaking step cannot be made until the support has also been immersed in the second soaking step and the catalase activity determined. Further, the concentration of cationic in the cationic-solvent solution apparently did not affect catalase activity of the support. Hence, a low concentration of cationic in solvent, on the order of 1% (weight/volume), was preferred.

When enzymes are immobilized on a support and a measurement of its activity is made, the measurement corresponds to the active enzyme on that support rather than the total amount of enzyme immobilized. Inactive enzyme on the support, that is, enzyme not functioning as a catalyst, is commonly deposited during the immobilization process, and the sum of the active and inactive enzyme corresponds to the total amount of enzyme deposited on the support. The nitrogen content of an enzyme-containing support may be correlated with the amount of enzyme immobilized on the support after the other sources of nitrogen in the supports tested, including residual N,N-bis(2-hydroxyethyl) tallowamine used in the manufacture of the Accurel ® porous polymer support and residual Duomeen ® C utilized in the first soaking step, are accounted for. To isolate the respective nitrogen contributions of these other sources and the enzyme, separate nitrogen analyses must be made. The first analysis is made prior to treatment with the enzyme, and the second after treatment with the enzyme. The difference between the two analyses corresponds to the amount of total (active and inactive) enzyme present.

The determination of total nitrogen content and enzyme content was made from the data compiled in Table II below. Support Nos. 1–8 are Accurel ® porous polymer.

TABLE II

| Support No. | Pretreatment | Catalase | % Duomeen ® C | % Catalase |
|---|---|---|---|---|
| 1 | None | No | | |
| 2 | SnCl₂ | No | | |
| 3 | SnCl₂ & Duomeen ® C | No | 1.6 | |
| 4 | Duomeen ® C | No | 1.8 | |
| 5 | None | Yes | | 2.8 |
| 6 | SnCl₂ | Yes | | 3.8 |
| 7 | SnCl₂ & Duomeen ® C | Yes | | 8.3 |
| 8 | Duomeen ® C | Yes | | 6.8 |

Specifically for the enzyme catalase, treatment with dihydrous stannous chloride increased the activity as indicated in the "% catalase" column of Table II, although no apparent improvement in storage stability resulted. Storage stability is a measure of the deterioration of enzyme activity over time; a support having high storage stability shows little enzyme activity deterioration over time, and vice-versa. Many other enzymes tested did not show an increase in enzyme activity after treatment of the support with stannous chloride or any other metal salt.

EXAMPLE 1

The support with the catalase immobilized thereon is prepared by the following process. As stated hereinabove, each enzyme's activity may or may not be enhanced by a particular pretreatment or process step. Catalase activity was enhanced by a metal salt, and the preferred immobilization process for catalase thus includes pretreatment with a metal salt. In the pretreatment step, the SnCl₂.2H₂O and the preferred salt solvent, acetone, are blended to form a dilute solution. In this embodiment, a 1% weight-volume (w/v) solution was prepared, but it did not appear that the concentration of salt was critical if the solution's concentration was between 0.1% (w/v) and 25% (w/v). Placing the Accurel ® porous polymer support in the dilute SnCl₂.2H₂O/acetone solution for between 5 and 10 minutes resulted in a support having a tin concentration of 500 ppm, as determined by atomic absorption. After removal from the solution, the support is rinsed with pure acetone.

Other metal salts were tested in lieu of stannous chloride dihydrate, including ferrous chloride dihydrate (FeCl₂.2H₂O). Pretreatment with FeCl₂.2H₂O resulted in a support having higher catalase activity than a support treated with SnCl₂.2H₂O, but the ferrous cation caused significant discoloration of the Accurel ® porous polymer film.

In the first soaking step, the metal salt-treated support is placed in a dilute solution of a diamine in a diamine solvent for between 10 and 60 minutes as the diamine solution is gently agitated. Diamine solvents may be selected from the group including chloroform, methanol, and isopropanol, among others, but chloroform is preferred for catalase on an Accurel ® porous polymer support. Amines, diamines, and quaternary ammonium salts may be selected from the group listed above in Table I. As may be seen from Table I, N-coco-1,3-diaminopropane is the most preferred nitrogen-containing compound for Accurel ® porous polymer on which catalase is immobilized. Again, a 1% (w/v) solution of diamine in solvent was used, and the concentration of the diamine was not deemed critical if the amine solution's concentration was between 0.1% (w/v) and 25% (w/v).

Prior to a second soaking step, which deposits the enzyme on the prepared support, the support is wetted with isopropanol or ethanol. The catalase used in this embodiment is deposited by means of a dilute aqueous solution. A solid catalase provided by Armour Pharmaceutical Co., Division of Revlon, Inc., Kankakee, Ill., or a catalase supplied in a buffered thymol saturated suspension provided by Miles Laboratories, Inc., Enzyme Products Division, Chicago, Ill. (Catalog #36-106), may be diluted with deionized water and used herein. Dilute aqueous solutions of catalase tested were at concentrations of between 0.1% (v/v) and 0.8% (v/v), and nearly identical activities of catalase on Accurel ® porous polymer film were noted when solutions at the ends of this range of concentration were used to deposit the enzyme on the support. The support is soaked with agitation in the dilute enzyme-water solution for a period in excess of four hours, and the catalase activity of the support increased with increasing soaking time. It is understood, however, that four hours is not a minimum time of immersion for the second soaking step and that the applicants have shown satisfactory enzyme activity may be realized in much less time, dependent upon, among other factors, support material used and the immersion time, solvent, and cationic used in the first soaking step. For example, the applicants have demonstrated that a second step soaking time of six minutes was sufficient to immobilize lipase on Accurel ® polypropylene porous polymer. At the end of the second soaking or immobilization step and prior to assaying the activity of the immobilized catalase, the support is removed from the aqueous enzyme solution and rinsed with several volumes of water to remove any soluble catalase on the surface.

In summary, then, the preferred method for immobilizing catalase on Accurel ® porous polymer film support is to subject the support to a pretreatment step in which it is immersed in a 1% (w/v) solution of SnCl₂.2H₂O in acetone for 5 minutes, rinsing the pretreated support with pure acetone, a first soaking step in which the support is soaked with agitation for from 10 up to about 60 minutes in a 1% (w/v) solution of Duomeen ® C (N-coco-1,3-diaminopropane) in chloroform, an isopropanol wetting of the support, and a second soaking step in which the support is soaked overnight with agitation in a 0.8% (w/v) aqueous catalase solution.

As stated above, this method provided optimal activity on this particular support and for this particular enzyme. Other enzymes and other porous supports may show optimal activity after being processed in a markedly different manner. Upon using this process for catalase on Accurel ® porous polymer, catalase loading on the support was found to be 8.3%, corresponding to an enzyme to support ratio of 1:11. In contrast, when simple adsorption was used to immobilize catalase on DEAE-cellulose, the loading was found to be 0.7%, corresponding to an enzyme to support ratio of 1:141. DEAE-cellulose is diethylamino-ethyl cellulose, a cellulose ether containing the group $(C_2H_5)_2NCH_2CH_2-$ bound to the cellulose in an ether linkage.

EXAMPLE 2

Glucose oxidase catalyzes the oxidation of β-D-glucose to gluconic acid and hydrogen peroxide. As any hydrogen peroxide produced lessens the activity of the glucose oxidase, catalase is co-immobilized on the support as part of a two enzyme system and as a hydrogen peroxide scavenger; an ideal support with potential in commercial gluconic acid production would have both enzymes immobilized thereon. The preferred method for immobilizing these two enzymes on a support, it will be seen, differs from that considered optimal for the catalase alone.

The activity of an enzyme on a substrate may be measured in International Units (IU) rather than Bakers as used in the catalase assay above. IU's have the dimensions "micromoles (μm) per minute," and correspond to micromoles of product formed per minute. In this embodiment, the product is gluconic acid and the support is selected from the the group including DEAE-cellulose; a porous glass; and Accurel ® porous polymer powder made of either Nylon 6, Nylon 11, or polypropylene. To immobilize glucose oxidase and catalase upon the powder, no pretreatment step was utilized, as none of the metal salts tested enhanced enzyme activity.

In the first soaking step, the untreated support powder is placed in a dilute solution of a diamine in a diamine solvent (1% (w/v) N-coco-1,3-diaminopropane in chloroform) for between 10 and 60 minutes as the solution is gently agitated.

After an isopropanol or denatured ethanol wetting of the powder support, a buffer solution is prepared for the two enzyme system. The buffer solution comprises 1.2 grams of sodium chloride and 1.2 grams of acetic acid in 400 milliliters of deionized water. As the preferred pH of a buffer solution for glucose oxidase immobilization is 6.0, a dilute sodium hydroxide solution is added to raise the pH of the buffer solution. Ten milliliters of glucose oxidase (catalog #31-618, from *Aspergillus niger*) and two milliliters of catalase (catalog #36-106, from bovine liver) both available from Miles Laboratories, Inc., Enzyme Products Division, Chicago, Ill., are then added to this buffer solution. The support was soaked in the dilute enzyme buffer solution for a period of not less than four hours. At the end of this second soaking step and prior to assaying the activity of the immobilized catalase, the support is removed from the buffer enzyme solution and rinsed with several volumes of water to remove any soluble enzyme on the surface.

The assay yielded the results shown in Table III below. In each case, the assay and immobilization were conducted using a 0.2 gram sample of the support. The conditions of the assay comprised using 75–100 milliliters of a 10% glucose substrate for up to 60 minutes.

TABLE III

| SUPPORT MATERIAL Accurel ® porous polymer powder: | mls SUBSTRATE | TIME OF ASSAY, MIN. | PERCENT GLUCONIC ACID IN REACTED SUBSTRATE | μMOLES GLUCONIC ACID FORMED | GLUCOSE OXIDASE ACTIVITY IU/GRAM ACCUREL ® POROUS POLYMER |
|---|---|---|---|---|---|
| polypropylene | 100 | 65 | 0.55 | 2,806 | 216 |
| polypropylene | 100 | 60 | 0.57 | 2,904 | 242 |
| Nylon 6 | 100 | 65 | 0.32 | 1,632 | 126 |
| Nylon 11 | 100 | 65 | 0.27 | 1,378 | 106 |
| polypropylene - | 100 | 60 | 0.54 | 2,760 | 230 |

The assay was conducted as follows: each of the supports listed in Table III was prepared as a glucose oxidase/catalase-containing, two-enzyme system. A substrate, that is, a solution containing the 10% β-D-glucose to be catalyzed, was contacted with the prepared support in an amount and for the number of minutes indicated in the table. Excess oxygen was maintained in the system by bubbling air through a sparger and into the closed system. The partially converted substrate was then analyzed by high pressure liquid chromatography (HPLC) for percent gluconic acid, and this figure was converted to μmoles of gluconic acid in accordance with the following equation, where (grams gluconic acid/milliliter substrate) = (percent gluconic acid/100):

$$(\text{milliliters substrate}) \frac{\frac{\text{grams gluconic acid}}{\text{milliliters substrate}}}{\text{MW gluconic acid}} \times$$

$$10^6 \frac{\mu\text{moles}}{\text{mole}} = \mu\text{moles gluconic acid in substrate}$$

The enzyme activity in International Units (IU) has the dimensions μmoles/minute, or amount of gluconic acid formed per minute. In each of the assays of Table III, 0.2 grams of support were used.

Three additional polypropylene tests were made. The first two polypropylene supports were not pretreated with a metal salt, but the last was pretreated in accordance with the procedure of Example 1 above. No significant difference was noted between the numerical average activity (IU/g) of the untreated supports (229) and the treated support (230).

EXAMPLE 3

Two tenths of a gram of Accurel ® porous polymer (polypropylene) powder support was placed in a solution of 100 ml of chloroform (HCCl₃) and one gram of Duomeen ® C for one hour in a first soaking step. The support was then removed from the bath and rinsed with chloroform. Prior to the second soaking step, the support is wetted with 3A ethanol, an ethanol denatured with approximately 5% methanol.

A buffer solution was prepared by adding to 50 ml of deionized water 0.15 grams of sodium phosphate dibasic and enough phosphoric acid ($H_3PO_4$) so as to adjust the pH to 7.0. Fifty milligrams of a solid urease provided by Sigma Chemical Company, P.O. Box 14508, St. Louis, Mo. 63178, as product number U4002, Type IX powder from Jack Beans, is added to the buffer solution. The wetted support is then placed in the buffered dilute urease solution and left therein overnight. At the end of ths second soaking step, the support is removed from the urease solution and rinsed with 500 ml deionized water to remove any soluble urease on the support's surface.

The assay was conducted by first preparing 100 ml of a substrate comprising an aqueous 3.0% (w/v) urea solution that also contained 0.3% of sodium phosphate buffer (dibasic) and enough phosphoric acid to adjust the pH to 7.0. The immobilized urease powder was added to the substrate and agitated for fifteen minutes with a magnetic stirrer. A dilution was then prepared at once by blending a two milliliter aliquot of this substrate-powder slurry with 100 ml deionized water and 1 ml of 10N sodium hydroxide solution. The amount of urease immobilized on the Accurel ® porous polymer powder support was determined by direct means. The ammonia formed by the immobilized urease is monitored by an Orion ammonia electrode, and is proportional to the urease activity of the powder as follows:

$$1 \text{ international unit} = 1 \text{ IU} = \frac{\mu\text{moles NH}_3 \text{ formed}}{\text{minute}}$$

The following Table IV indicates the results of the assay at 15 minutes using three samples of Accurel ® porous polymer:

TABLE IV

Urease Activities with Duomeen ® C as first soaking step cationic

| Accurel Sample No. | Material | Activity, IU per gram Accurel ® Porous Polymer |
|---|---|---|
| 1490-21-1 | Polypropylene | 2,333 |
| 1490-30-1 | Polypropylene | 2,933 |
| 1448-106-1 | Nylon 6 | 1,333 |

EXAMPLE 4

Two tenths of a gram of Accurel ® porous polymer (polypropylene) powder support was placed in a solution of 100 ml of acetone and one gram of Arquad ® 2C for one hour in a first soaking step. The support was then removed from the bath and rinsed with acetone. Prior to the second soaking step, the support is wetted with 3A ethanol, an ethanol denatured with approximately 5% methanol.

A buffer solution was prepared by adding to 50 ml of deionized water 0.3 grams of sodium chloride, and 0.22 grams of sodium acetate trihydrate, a buffer and the pH is then adjusted to 7.0 with an appropriate amount of acetic acid ($CH_3COOH$). Fifty milligrams of a solid urease provided by Sigma Chemical Company, P.O. Box 14508, St. Louis, Mo. 63178, as product number U4002, Type IX powder from Jack Beans, is added to the buffer solution. The wetted support is then placed in the buffered dilute urease solution and left therein overnight. At the end of this second soaking step, the support is removed from the urease solution and rinsed with 500 ml deionized water to remove any soluble urease on the support's surface.

The assay was conducted by first preparing 100 ml of a substrate comprising an aqueous 3.0% (w/v) urea solution that also contained 0.3% of sodium phosphate dibasic and enough phosphoric acid to adjust the pH to 7.0. The immobilized urease powder was added to the substrate and agitated for fifteen minutes with a magnetic stirrer. A dilution was then prepared at once by blending a two milliliter aliquot of this substrate powder slurry with 100 ml deionized water and 1 ml of 10N sodium hydroxide solution. The amount of urease immobilized on the Accurel ® porous polymer powder support was determined by direct means. The ammonia formed by the immobilized urease is monitored by an Orion ammonia electrode, and is proportional to the urease activity of the powder as follows:

$$1 \text{ international unit} = 1 \text{ IU} = \frac{\mu\text{moles NH}_3 \text{ formed}}{\text{minute}}$$

The following Table V indicates the results of the assay at 15 minutes using two samples of Accurel ® porous polymer:

TABLE V

Urease Activities with Arquad ® 2C as first soaking step cationic

| Accurel Sample No. | Material | Activity, IU per gram Accurel ® Porous Polymer |
|---|---|---|
| 1494-122-1 | Polypropylene | 1,100 |
| 1494-126-1 | Polypropylene | 1,367 |

EXAMPLE 5

A 1% (w/v) solution of Arquad ® 2C-75 (the quaternary dimethyldicocoammonium chloride, 75% active) in acetone was prepared by blending 20 grams of the quaternary and two (2) liters of acetone in a glass beaker. In a first soaking step, forty (40) grams of the Accurel ® Nylon 6 porous polymer powder was immersed in the quaternary-acetone solution for sixty minutes with agitation provided by a magnetic stirrer. The powder was then filtered on a Buchner funnel, rinsed with 0.5 to 1.0 liters of fresh acetone, and air dried in a glass dish for 1–2 hours.

Human chorionic gonadoptropin (HCG) is a protein; specifically it is a hormone released only by pregnant women, and detection thereof is thus the basis of pregnancy tests. Three solutions of HCG were prepared by blending HCG, thimerosal (ethylmercurithiosalicylic acid sodium salt, a preservative), and deionized water as follows:

TABLE VI

| SOLUTION | [1]HCG (grams) | Thimerosal (grams) | Deionized water (milliliters) | Con'n HCG % (w/v) |
|---|---|---|---|---|
| A | 0.75 | 0.075 | 375 | 0.2 |
| B | 0.150 | 0.150 | 750 | 0.02 |
| C | 0.030 | 0.300 | 1,500 | 0.002 |

[1]The HCG was obtained from Organon Inc., 43 Route 46, Pine Brook, New Jersey 07058.

In the second soaking step, immobilization of the hormone was effected by placing five (5) grams of the Arquad ® 2C-treated Accurel ® Nylon 6 powder in Solution A overnight with agitation. The powder was then removed from the solution by filtration on a Buchner funnel, and rinsed with two to three liters of deionized water. The powder was finally dried over vacuum for 15–30 minutes and air dried for three to four hours.

Two other portions of the support were obtained from the forty gram sample originally prepared in the first soaking step and immersed in the other two HCG solutions. Specifically, ten (10) grams of Arquad® 2C-treated support was placed in solution B overnight with agitation and twenty (20) grams of Arquad® 2C-treated support was placed in solution C overnight with agitation. Both of these portions were filtered and dried as described above.

Solutions A, B, and C were formulated with the intention of preparing supports having loading levels of 10%, 1.0%, and 0.1%, respectively. The supports immersed in solutions A and B had measured loadings of 7.8% and 1.0%. The support immersed in solution C had a measured loading of somewhat less than 0.1%, and could not be precisely determined because 0.1% was the lower limit of detection for this analysis. HCG loadings on these supports were calculated indirectly by determining the difference between HCG levels in the solutions prior to and after immobilization. The difference corresponded to the amount of HCG immobilized on the nylon powder.

What is claimed is:

1. A method of immobilizing a protein on a porous polymeric support, comprising a first soaking step in which said support is placed in a dilute solution of a long-chain cationic comprising a nitrogen compound having at least one alkyl or alkenyl group containing at least eight carbon atoms attached thereto in a solvent, said support being gently agitated during said first soaking step, and a second soaking step in which said support is soaked in a dilute aqueous solution of said protein.

2. The method as set forth in claim 1, wherein said support is placed in said dilute solution of a cationic in a solvent for between 5 and 60 minutes and wherein said support is soaked for more than four hours in said second soaking step.

3. The method as set forth in claim 1, wherein said protein is a hormone.

4. The method as set forth in claims 1, 2, or 3, wherein said long-chain cationic is the diamine N-coco-1,3-diaminopropane.

5. The method as set forth in claim 3, wherein said hormone is human chorionic gonadotropin.

6. A method of immobilizing a hormone on a support, comprising a first soaking step in which said support is placed in a dilute solution of a diamine having at least one alkyl or alkenyl group containing at least eight carbon atoms attached thereto in a solvent for said diamine for between 5 and 60 minutes, said diamine solution being gently agitated during said first soaking step, and a second soaking step in which said support is soaked in a aqueous solution of said hormone, said aqueous solution having a concentration of said hormone of from 0.002% (w/v) to 0.2% (w/v).

7. A method of immobilizing an enzyme on a porous polymeric support, comprising a first soaking step in which said support is placed in a dilute solution of a long-chain cationic comprising a nitrogen compound having at least one alkyl or alkenyl group containing at least eight carbon atoms attached thereto in a solvent, said support being gently agitated during said first soaking step, and a second soaking step in which said support is soaked in a dilute aqueous solution of said enzyme.

8. The method as set forth in claim 7, wherein said support is placed in said dilute solution of said long-chain cationic in a solvent for between 10 and 60 minutes and wherein said support is soaked for more than four hours in said second soaking step.

9. The method as set forth in claim 8, wherein said solvent is acetone.

10. The method as set forth in claims 7, 8, or 9, wherein said long-chain cationic is N-coco-1,3-diaminopropane.

11. The method as set forth in claim 7, wherein said enzyme is a two enzyme system of catalase and glucose oxidase.

12. The method as set forth in claim 8, wherein said enzyme is a two enzyme system of catalase and glucose oxidase.

13. The method as set forth in claim 9, wherein said enzyme is a two enzyme system of catalase and glucose oxidase.

14. The method as set forth in claim 10, wherein said enzyme is a two enzyme system of catalase and glucose oxidase.

15. A method of immobilizing catalase on a porous polymeric support, comprising a pretreatment step in which said support is placed in a dilute solution of a metal salt in a salt solvent for between 5 and 10 minutes, rinsing said support with said salt solvent or another salt solvent, a first soaking step in which said support is placed in a dilute solution of a diamine having at least one alkyl or alkenyl group containing at least eight carbon atoms attached thereto in a solvent for said diamine for between 10 and 60 minutes, said diamine solution being gently agitated during said first soaking step, and a second soaking step in which said support is soaked with agitation in a 0.8% (w/v) aqueous catalase solution.

16. The method as set forth in claim 15, wherein said salt solvent is acetone.

17. The method as set forth in claim 15, wherein said amine solvent is acetone.

18. The method as set forth in claim 16, wherein said amine solvent is acetone.

19. The method as set forth in claim 18, wherein said metal salt is $SnCl_2.2H_2O$.

20. The method as set forth in claim 18, wherein said metal salt is $FeCl_2.2H_2O$.

21. The method as set forth in claims 19 or 20, wherein said diamine is N-coco-1,3-diaminopropane.

22. The method as set forth in claim 21, wherein said enzyme is catalase.

23. A method of immobilizing catalase on a porous polymeric film support, comprising a pretreatment in which said support is placed in a 1% (w/v) metal salt solution of $SnCl_2.2H_2O$ in acetone; removing said support from said metal salt solution after five minutes and rinsing said support with acetone; a first soaking step in which said support is immersed for 60 minutes in a 1% (w/v) diamine solution of N-coco-1,3-diaminopropane in chloroform; removing said support from said diamine solution and wetting said support with isopropanol; and a second soaking step in which said support is immersed for more than four hours in a 0.8% (v/v) aqueous catalase solution.

24. A method for immobilizing glucose oxidase and catalase on a porous polymer powder support, comprising: a first soaking step in which said support is immersed for 10 minutes in a 1% (w/v) diamine solution of N-coco-1,3-diaminopropane in chloroform; removing said support from said diamine solution and wetting said support; and a second soaking step in which said support is immersed for more than four hours in a dilute buffer solution of 2.5% (v/v) glucose oxidase and 0.5% (v/v) catalase in deionized water.

25. The method as set forth in claims 1, 2, 3 or 7 wherein said long-chain cationic is selected from the group consisting of amines, diamines, and quaternary ammonium compounds.

26. The method as set forth in claim 25, wherein said long-chain cationic is a diamine.

27. The method as set forth in claims 1, 6, 15, 23 or 24, wherein said support comprises polypropylene.

28. The method as set forth in claim 10, wherein said support comprises polypropylene.

* * * * *